United States Patent
Sasaki et al.

[11] Patent Number: 5,877,381
[45] Date of Patent: *Mar. 2, 1999

[54] PARTICULATE CATALYST FOR USE IN A FLUIDIZED BED

[75] Inventors: Yutaka Sasaki; Hiroshi Yamamoto, both of Yokohama; Kiyoshi Moriya, Hayama; Yoshimi Nakamura, Yokohama, all of Japan

[73] Assignee: Nitto Kagaku Kogyo Kabushiki Kaisha, Tokyo-to, Japan

[*] Notice: This patent issued on a continued prosecution application filed under 37 CFR 1.53(d), and is subject to the twenty year patent term provisions of 35 U.S.C. 154(a)(2).

[21] Appl. No.: 673,053

[22] Filed: Jul. 1, 1996

[30] Foreign Application Priority Data

Jun. 30, 1995 [JP] Japan ..................... 7-165576
Jun. 5, 1996 [JP] Japan ..................... 8-142887

[51] Int. Cl.$^6$ ................. C07C 5/327; C07C 255/00; C07C 47/00; C07C 5/02
[52] U.S. Cl. ............... 585/658; 502/503; 502/305; 502/308; 502/325; 502/326; 502/327; 502/349; 502/353; 568/420; 568/780; 568/579; 558/303; 585/654; 585/250
[58] Field of Search ................. 502/503, 305, 502/308, 325, 326, 327, 349, 353; 568/420, 780, 579; 558/303; 585/658, 654, 250

[56] References Cited

U.S. PATENT DOCUMENTS 4,392,987  7/1983  Laine et al. ............... 252/448
4,410,448  10/1983  Shaw et al. ............... 502/503
5,132,269  7/1992  Sasaki et al. ............... 502/205

FOREIGN PATENT DOCUMENTS 0153077  8/1985  European Pat. Off. .
0154408  9/1985  European Pat. Off. .
8-141401  6/1996  Japan .

OTHER PUBLICATIONS

Shimadzu, Micro Compression Testing Machines, MCTM/MCTE Series, "Effective Tool For Testing Compression Strength Of Fine Particles, Fibers, and Micro Structures", C227–E001A (no month).

Primary Examiner—Walter D. Griffin
Assistant Examiner—Nadine Preisch
Attorney, Agent, or Firm—Wenderoth, Lind & Ponack, L.L.P.

[57] ABSTRACT

The present invention provides a fluidized bed catalyst for the synthetic reaction of organic compounds which has a reduced catalyst loss. A fluidized bed catalyst for organic compound synthetic reaction, characterized in that 90% or more of the catalyst particles is in the range of 5–500 μm on the weight-based particle size distribution and 90% or more of the 20–75 μm particles has a crushing strength which satisfies the following equation:

$$CS > A \cdot d_\alpha$$

wherein CS represents a crushing strength [g-weight/particle],

A represents a constant 0.001, d represents a particle diameter [μm], and

α represents a constant 2.

20 Claims, No Drawings

5,877,381

PARTICULATE CATALYST FOR USE IN A FLUIDIZED BED

BACKGROUND OF THE INVENTION

1. Field of the Invention

The present invention relates to a particulate catalyst for use in a fluidized bed in a vapor phase reaction, which catalyst is endowed with an extensively reduced loss of catalyst particles, particularly, those having a smaller particle size, and can suppress the reduction of the yield of a desired product due to the deterioration of the fluidized state of a fluidized bed.

2. Background Art

Particulate catalysts employed in reactions of a vapor phase in a fluidized bed are generally required to be excellent in catalyst strength as well as catalyst activity. As the test of the strength of a fluidized bed catalyst, a test method of attrition-resistant properties in accordance with the ACC method (American Cyanamid Co. Ltd. 6/31-4m-1/57, "Test Method for Synthetic Fluid Cracking Catalyst") has been used. The values of the attrition-resistant properties according to this test method have been used as a standard for judging the applicability of a catalyst to a fluidized bed reaction, that is the degree of catalyst loss in a reactor. In their applications to practical reactor, the attrition-resistant properties, however, do not always correspond to the loss of a catalyst.

Furthermore, there have been proposed a variety of explanations for the main cause of loss of particulate catalysts. None of these explanations have become established theory. Among them, there have been proposed, as the main cause of catalyst loss, the crushing or attrition of catalyst particles due to the jet gas flow at spargers of a reactor, or the collision or attrition between catalyst particles with each other, and between catalyst particles and a reactor wall or internal components.

However, irrespective of the causes, it is the inventors' belief that catalyst particles in a fluidized bed reactor tend to be crushed or worn more easily if the particles have a finer particle size, so that the strength of particles having a smaller diameter is particularly important and has to be taken into consideration in order to reduce the catalyst loss. However, as far as the present inventors know, no improvements of techniques have been proposed regarding this point.

By way of example, while the strength of a single catalyst particle alone is referred to in Japanese Patent Laid-Open Publication No. 262753/1993, nothing is indicated about the strength of the finer particles or the catalyst loss with only exception of the breaking load of particles having a particle size of 88 to 150 μm. Also, only the crushing strength of a catalyst is described in Examples of Japanese Patent Laid-Open Publication No. 144132/1995.

The object of the present invention is to provide such a particulate catalyst for use in a fluidized bed that the catalyst loss can be reduced whereby the particle size distribution can be maintained in an appropriate range and the reaction can also be maintained at a high level without lowering the contact efficiency.

SUMMARY OF THE INVENTION

The present invention intends to solve the above described problems.

The particulate catalyst for use in a fluidized bed in reactions for syntheses of organic compounds is characterized according to the invention by the particle properties such that 90% or more of the catalyst particles are in the range of 5 to 500 μm on the weight-based particle size distribution and 90% or more of the 20 to 75 μm particles have a crushing strength in terms of a breaking load which satisfies the following equation:

$$CS > A \cdot d^{\alpha}$$

wherein CS represents a crushing strength in terms of a breaking load [g-weight/particle],
A represents a constant 0.001,
d represents a particle diameter [μm], and
α represents a constant 2.

According to the present invention, the catalyst loss of a fluidized bed catalyst can be reduced. Thus, the particle size distribution of the fluidized bed catalyst can be maintained in a proper range, and the reaction can be maintained at a high level without lowering the contact efficiency. Specifically, according to the present invention, a preferred vapor phase fluidized bed catalyst can be provided in which the strength of the catalyst particles is defined for the practically important particles having small particle diameters and thus the catalyst loss is extensively reduced.

DETAILED DESCRIPTION OF THE PREFERRED EMBODIMENT OF THE INVENTION

<General description>

There has been generally recognized the importance of the particle size distribution of a catalyst, particularly the presence of particles having small particle diameters, in order to maintain a good fluidized state in a catalytic vapor phase fluidized bed process (see e.g. T.MIYAUCHI, S. FURUSAKI, S. MOROOKA and Y. IKEDA, "Transport Phenomena and Reaction in Fluidized Catalyst Beds", Advances in Chemical Engineering, Vol. 11, (1981), Academic Press). As described in this literature, about 10 to 40% by weight of the particles having a particle size of 44 μm or less is required for obtaining a good fluidized state, the average particle diameter is generally in the range of 50 to 70 μm, and the bulk density is generally in the range of about 0.4 to 1.2 g/ml.

Industrial fluidized bed reactors are generally equipped with built-in cyclones for collecting catalyst particles to escape. In such a fluidized bed reactor, catalyst particles are separated from the effluent gas by the cyclone, circulated to the reactor bottom through a dip-leg, and fine particles which cannot be collected by the cyclone will be discharged from the reactor. Moreover, the smaller the particle diameter is, the lighter the particles become, and thus fine particles having smaller particle diameters are present in more amount around the cyclone of the reactor, so that the particles having smaller particle diameters are circulated more times through the cyclone.

The present inventors have examined extensively the causes of catalyst loss in the fluidized bed reactor. As a result thereof, they have found that the main causes of catalyst loss are not the crushing or attrition of the particles due to the jet flow around the sparger nozzles or the collision or attrition between catalyst particles or between the particles and a reactor wall or internal components of the reactor, but the catalyst loss is caused in a higher proportion by the collision of catalyst particles against the cyclone, particularly the inlet part or internal wall of the cyclone and is remarkable especially when crushing strength, particularly the crushing strength of the fine particles, is small.

By the way, the general tendency that the particles having a smaller particle diameter have a smaller value of the breaking load is known. By way of example, it has been described that spherical particles have a breaking load, empirically in proportion to about the 1.8th to 2.0th power of the particle diameter, and the higher the homogeniety and the larger the diameter of the particles are, the more the proportionality is increased (J. F. LE PAGE and J. MIQUEL, Preparation of Catalysts, edited by B.Delmon, P. A. Jacobs and C.Poncelet, 1976, Elsevier Scientific Publishing Co.). However, the measurements reported were conducted on rather large granules having a diameter of several millimeters or more and the experimental equation was obtained thereon.

As far as the present inventors know, no discussions of the relationship between the particle diameter and crushing strength of catalyst particles having a particle size of a micron order have been known.

The particles to which the present invention is directed are those of particulate catalyst for fluidized bed operation having small particle diameters of a micron order, for example, in the range of 20 to 75 $\mu$m. According to our knowledge, it would be rather seldom that conventional catalyst particles for a fluidized bed are homogeneous over a wide range of particle diameters. The present invention is just based on this point, such that particulate catalysts should have a certain particle size distribution whereby the crushing strength must be practically determined and judged on the particular catalyst particles in the range where industrial problems tend to occur.

It has been thus considered that the strength of particles having a smaller particle diameter should be noted as for the loss of a fluidized bed catalyst during the reaction.

<Physical properties of particulate catalyst for the fluidized bed operation>

The fluidized bed catalyst according to the present invention is characterized in that 90% or more, preferably 95% or more of the 20 to 75 $\mu$m particles have a crushing strength in terms of a breaking load which satisfies the following equation, $CS > A \cdot d^{\alpha}$, wherein CS represents a crushing strength in terms of a breaking load [g-weight/particle], A represents a constant 0.001; d represents a particle diameter [$\mu$m]; and a represents a constant 2.

In recent years, apparatuses which can be used are commercially available as the measuring apparatus of the crushing strength of such particles having a small particle diameter. There are several appropriate apparatuses, and the crushing strength (CS) defined in the present invention should have a value measured with "Shimadzu MCTM-200" manufactured by Shimadzu Seisakusho, Ltd., Japan under the following measuring conditions:

Indenter
 Upper pressurizing indenter, 500 $\mu$m plain indenter made of diamond;
 Lower pressurizing plate, SUS plate;
Loading rate: 0.72 g weight/sec.

Furthermore, the 20 to 75 $\mu$m particles means that the particle has a diameter or an average of the length and breadth of the particle in the range of 20 to 75 $\mu$m, and may be obtained specifically by screening particles with micro mesh high precision sieves manufactured by Buckbee Mears. Co., St. Paul, U.S.A. The particles are those randomly sampled from the 20 to 75 $\mu$m particles in a statistically significant amount.

The fluidized bed catalyst according to the present invention is characterized in that 90% or more, preferably 95% or more of the catalyst particles are in the range of 5 to 500 $\mu$m, preferably 10 to 200 $\mu$m on the weight-based particle size distribution.

Even if the catalyst particles have the particle size distribution within the above described range, the catalyst loss becomes large and causes problems in practical use in the case where more than 10 of the 20 to 75 $\mu$m particles do not satisfy the above described equation for the crushing strength (CS). In this case, the catalyst loss tends to be larger when the ratio of the particles which do not satisfy the equation is increased.

<Chemical aspects of the fluidized bed catalyst/object reactions>

The catalyst according to the present invention is a particulate catalyst used in a fluidized bed reactor for organic compound synthetic reactions in vapor phase.

The "organic compound synthetic reactions" herein includes oxidation, ammoxidation, oxidative dehydrogenation, and dehydrogenation; and dehydration, alkylation, and hydrogenation.

A preferred embodiment of the organic compound synthetic reactions is an oxidation reaction. The "oxidation reaction" herein should be understood to have the widest meanings including an oxidation reaction for introducing an oxygen atom into an organic compound, an oxidation reaction for depriving a hydrogen atom from an organic compound, i.e. a dehydrogenation reaction, an oxidative dehydrogenation for conducting dehydrogenation oxidatively, and an ammoxidation reaction for producing a nitrile by conducting oxidation reaction in the presence of ammonia.

Particularly, the oxidation of a $CH_3$ group adjacent to an ethylenic double bond or aromatic double bond in one or two step oxidation into a CHO group or COOH group, and the transformation of the $CH_3$ group into a CN group which is the oxidation in the presence of ammonia, viz. ammoxidation, are preferred.

Examples of such oxidation reactions include the following reactions.

(a) As the oxidation reactions, oxidation of olefins, preferably those having 2 to 5 carbon atoms, e.g. the oxidation of propylene, 1-butene, 2-butene and isobutene into acrolein, maleic anhydride, crotonaldehyde, methacrolein, acrylic acid and methacrylic acid; oxidation of alkylaromatics wherein the term "aromatics" includes heteroaromatics, such as oxidation of methylbenzene, dimethylbenzene, methylpyridine, and dimethylpyridine into benzaldehyde, benzoic acid, diformylbenzene, benzene dicarboxylic acid, phthalic anhydride, pyridinecarboxylic acid, diformylpyridine, and pyridine dicarboxylic acid; oxidation of aldehydes such as oxidation of acrolein and methacrolein into acrylic acid and methacrylic acid; and oxidation of alkanes, such as oxidation of n-butane into maleic anhydride.

(b) As the ammoxidation reactions, ammoxidation of olefins, such as ammoxidation of propylene, 1-butene, 2-butene and isobutene into acrylonitrile, maleimide, crotononitrile and methacrylonitrile; ammoxidation of alkylaromatics such as ammoxidation of methylbenzene, dimethylbenzene, methylpyridine and dimethylpyridine into cyanobenzene, dicyanobenzene, cyanopyridine and dicyanopyridine; ammoxidation of 2,6-dichlorotoluene into 2,6-dichlorobenzonitrile; ammoxidation of alcohols such as ammoxidation of methanol into hydrogen cyanide; and ammoxidation of alkanes, such as ammoixation of propane into acrylonitrile.

(c) As the oxidative dehydrogenation reaction, oxidative dehydrogenation of alkanes such as oxidative dehydrogenation of propane and butane into propylene and butene; oxidative dehydrogenation of ethylbenzene into styrene and oxidative dehydrogenation of olefins such as oxidative dehydrogenation of butene into butadiene.

The dehydrogenation reactions include the synthesis of cyclohexanone by the dehydrogenation of cyclohexanol, the synthesis of formaldehyde by the dehydrogenation of methanol, the synthesis of methyl formate by the dehydrogenation of methanol.

The alkylation reactions include the methylation of phenols by methanol, e.g. the synthesis of o-cresol and 2,6-xylenol, and the synthesis of alkylamines by the reaction of an amine with an alcohol.

The hydrogenation reactions include the synthesis of aniline by the hydrogenation of nitrobenzene, the synthesis of amines by the hydrogenation of a nitrile, e.g. the synthesis of propylamine by the hydrogenation of propionitrile, the synthesis of an aromatic aldehyde by the hydrogenation of an aromatic carboxylic acid, e.g. the synthesis of benzaldehyde by the hydrogenation of benzoic acid, and the synthesis of tetrahydrofuran and 1,4-butanediol by the hydrogenation of maleic anhydride and γ-butyrolactone.

The dehydration reactions includes the synthesis of ethers by the dehydration of alcohols, e.g. the synthesis of dimethyl ether, ethyl ether and methyl tert-butyl ether, the synthesis of amines or anilines by the reaction of alcohols or phenols with ammonia.

The catalysts which promote the organic compound synthetic reaction as described above are well-known, and a variety of the catalysts will be the object of the present invention as far as they have the above described physical properties.

The catalysts as the object of the present invention on the basis of their chemical properties are those comprising transition metal compounds, poly acids or their salts, such as, for example molybdates, e.g. bismuth phosphomolybdate; oxides of antimony and vanadium; or solid acids or solid base catalysts, e.g. catalysts comprising silica, alumina, silica-alumina, zirconia, titania and magnesia.

On the other hand, the composition of the catalyst as the object of the present invention is represented by the following empirical formulae on the basis of its constituent elements. These formulae have conventionally been used for the composite oxide catalysts of these types, which, however, will not guarantee the bonding structure of elements as shown in these formulae.

Empirical formula (1):

$Sb_{10}A_aB_bC_cO_x$ (atomic ratio)

wherein A is at least one element selected from the group consisting of Fe, Co, Ni, Mn, U, Ce, Sn and Cu, preferably at least one element selected from the group consisting of Fe, U, Sn and Cu;

B is at least one element selected from the group consisting of V, Mo and W;

C is at least one element selected from the group consisting of Mg, Ca, Sr, Ba, La, Ti, Zr, Nb, Ta, Cr, Re, Ru, Os, Rh, Ir, Pd, Pt, Ag, Zn, Cd, B, Al, Ga, In, Tl, Ge, Pb, P, As, Bi, Se and Te, preferably at least one element selected from the group consisting of Mg, La, Nb, Ag, Zn, B, Pb, P, Bi and Te;

a is 1 to 10;

b is 0 to 5;

c is 0 to 10;

Empirical formula (2):

$Mo_{10}D_dE_eF_fO_x$ (atomic ratio)

wherein D is at least one element selected from the group consisting of Fe, Ni, Co, Mn, Cr, Mg, Ca, Cu, Zn, La, Ce, Al and Sn, preferably at least one element selected from the group consisting of Fe, Ni, Co, Mn, Cr, Mg and Ce;

E is at least one element selected from the group consisting of Sb, Bi, As, P, B, Te, W and V;

F is at least one element selected from the group consisting of Li, Na, K, Rb and Cs;

d is 0 to 10;

e is 0 to 10;

f is 0 to 3; and

Empirical formula (3):

$V_{10}G_gH_hO_x$ (atomic ratio)

wherein G is at least one element selected from the group consisting of Li, Na, K, Rb, Cs, Tl, Mg, Ca, Sr and Ba, preferably at least one element selected from the group consisting of K, Rb, Cs and Mg;

H is at least one element selected from the group consisting of La, Ce, Ti, Zr, Nb, Ta, Cr, Mo, W, Mn, Re, Fe, Ru, Os, Co, Rh, Ir, Ni, Pd, Pt, Cu, Ag, Zn, Cd, B, Al, Ga, In, Ge, Sn, Pb, P, As, Sb, Bi, S, Se and Te, preferably at least one element selected from the group consisting of La, Ce, Nb, Cr, Mo, W, Mn, Fe, Co, Ni, P, Sb, Bi and Te;

g is 0 to 5; and h is 0 to 15.

In those formulae (1) to (3), O indicates oxygen atom, and x indicates the number of the oxygen atom in the oxide formed by the elements concerned.

Particularly preferred ones among these catalysts are those for oxidation or ammoxidation represented by the empirical formula (1) or (2).

<Production of the fluidized bed catalyst>

While the catalysts for use in a fluidized bed for vapor phase reactions according to the present invention can be produced basically by the methods known as the methods for preparing catalysts for a fluidized bed which are conventionally used for each of the reactions, consideration on more limited composition and preparation method is required practically.

Also, the method for preparing catalysts includes a method for preliminarily preparing a carrier, on which catalyst ingredients are supported. In this case, the strength of the catalyst tends to be dependent on the strength of the carriers used. It is thus important to select a type of carrier in due consideration of the present invention.

The methods for producing the fluidized bed catalysts used for the oxidation and ammoxidation of olefins are disclosed in Japanese Patent Publication No. 12913/1979 and U.S. Pat. No. 3,044,965 and U.S. Pat. No. 3,746,657 for Mo-based catalysts, and U.S. Pat. No. 3,341,471, U.S. Pat. No. 3,657,155 and U.S. Pat. No. 3,686,138 for Sb-based catalysts.

Also, the methods for producing the fluidized bed catalysts used for synthesizing maleic anhydride by the oxidation of butanes or butenes are disclosed in GB 1285075 and U.S. Pat. No. 4,647,673 for V, P-based catalysts.

The methods for producing the fluidized bed catalysts for synthesizing aldehydes, acid anhydrides or nitriles or the like by the oxidation or ammoxidation of an alkyl aromatic hydrocarbon, an alkyl heteroaromatic hydrocarbon, or a saturated hydrocarbon, or those for alkylation are disclosed in GB 1246108 and U.S. Pat. No. 4,517,389 for V-based catalysts.

It is not always satisfactory as the method for preparing a fluidized bed catalyst satisfying the requirements of the present invention to simply follow the methods described in the above patents, and the more limited compositions and production methods or process are generally required.

A fluidized bed catalyst is generally prepared through (1) a process of preparing a catalyst slurry, (2) a process of spray-drying, and (3) a process of calcination.

In the production of a catalyst slurry, raw materials, blending sequences, the ranges of pH and temperature must be so selected as to be suited for the object of the present invention. The process for preparing the catalyst slurry often involves precipitation reactions, so that the pH and temperature conditions should be provided by sufficient blending and agitation and in consideration of the shift of equilibrium which tends to occur.

In the spray-drying process, it is required to set the pumping rate of the catalyst slurry, the drying gas volume into the spray-drier, the inlet temperature and the outlet temperature in consideration of the property of the slurry subjected to spray-drying, that is the composition, concentration and viscosity of the slurry, and the ease of drying the spray-dried product. When the temperature is too high, evaporation rate becomes excessively high thus lowering the strength or pulverizing the product. On the other hand, when the temperature is too low, the physical property is deteriorated or the yield is lowered due to the irregular shapes caused by the coalescence of the particles or the adhesion of particles to the wall of the spray-drier.

Furthermore, calcination process is also important as the final process for determining the properties of the catalyst formed. If the calcination temperature is too low, the product is sometimes not sintered satisfactorily thus resulting in a poor strength. If the calcination is conducted at an excessively high temperature, volatile ingredients sometimes evaporate thus resulting in the lowering of the strength, or the particles adhere to each other due to the separating-out or the melting of the ingredients thus resulting in the promotion of the agglomeration or the lowering of the strength due to the crystal growth.

Also, the method of calcination is important, and fluidized bed calcination is appropriate for homogeneous and uniform calcination. In the stationary calcination in a box type furnace or a tunnel furnace, temperature difference is generated between the upper layer and the lower layer, so that inhomogeneities in calcination tend to occur and the temperature of a part of the mass under calcination is excessively lower or higher than the set temperature for obtaining the satisfactory strength. Also, even in a rotary calciner, attention must be paid to avoid uneven calcination from place to place in the furnace.

Thus, the calcination process requires the setting of the optimum conditions for controlling the temperatures, and the setting and controlling the calcination temperature strictly, for the given calcination methods used.

The present invention is described in detail below with reference to non-limiting examples.

EXAMPLE 1

The synthetic reactions of acrylonitrile (AN) by the ammoxidation of propylene were carried out under the same conditions with Catalyst A [composition (atomic ratio): $Fe_{11.5}Sb_{25}Cu_{3.0}Te_{2.0}Mo_{1.0}O_{77.25}(SiO_2)_{60}$] and Catalyst B [composition (atomic ratio): $Fe_{13}Sb_{25}Cu_{3.5}Te_{1.5}W_{0.4}MO_{0.5}O_{78.7}(SiO_2)_{60}$] in a fluidized bed reactor having a diameter of 3 m. The Catalysts A and B, respectively, comprise 90% or more of the particles having a particle size in the range of 10 to 200 $\mu$m. The bulk density of the catalysts, the results of the attrition test according to the ACC method, and the results of the crushing strength test according to the present invention, and the catalyst loss are shown in Table 1.

TABLE 1

| Catalyst | Bulk density [g/ml] | Attrition test*(1) | Crushing strength test*(2) | Catalyst loss [kg/t · AN]*(3) |
|---|---|---|---|---|
| A | 0.90 | 0.5 | content of 20 to 75 $\mu$m particles having a crushing strength of 0.001 × $d^2$ [g-weight/particle] or more: 92% | 0.6 |
| B | 1.10 | 0.8 | content of 20 to 75 $\mu$m particles having a crushing strength of 0.001 × $d^2$ [g-weight/particle] or more: 97% | 0.2 |

The Catalysts A and B used in this example were prepared in the manner as follows.

Catalyst A (corresponding to Empirical formula (1)):

402 kg of antimony trioxide is weighed. (I)

70.8 kg of electrolytic iron powder is weighed. 507 liters of nitric acid (sp. gr. 1.38) and 317 liters of water are mixed and heated. The iron powder is added to the mixture portionwise and dissolved. 80 kg of copper nitrate is weighed, added to the iron nitrate solution formed above and dissolved. (II)

19.7 kg of ammonium paramolybdate is dissolved in 187 liters of water. Next, 50.7 kg of telluric acid $H_6TeO_6$ was added and dissolved. (III)

1990 kg of silica sol ($SiO_2$, 20% by weight) is weighed. (IV)

(III), (II) and (I) are added to (IV) in this sequence, and 15% aqueous ammonia is added portionwise to the mixture with thorough stirring. An ultrasonic oscillator is set, and pH was adjusted to 2.3 under the ultrasonic wave irradiation.

The slurry thus obtained is stirred throughly and heated to 98° C. for 3 hours in a stainless steel vessel equipped with a reflux condenser.

Next, the slurry is adjusted to a concentration of about 20% by weight (based on oxides), and spray-dried with a nozzle type spray-drier at an outlet temperature of 160° C. Fine spherical particles thus obtained are calcined at 250° C. for 8 hours, then at 400° C. for 16 hours, finally calcined in air at 740° C. for 5 hours in fluidized bed calciner under fluidization at a gas linear velocity of 20 cm/sec.

Catalyst B (corresponding to Empirical formula (1)):

In the same manner as for the Catalyst A except that ammonium paratungstate is used as the raw material for tungsten, a predetermined amount of the paratungstate is dissolved in water, added to the ammonium paramolybdate solution, and the telluric acid is then added to form a solution.

The final calcination is at 810° C. for 5 hours after the calcination at 400° C. for 16 hours.

COMPARATIVE EXAMPLE 1

The synthetic reaction of acrylonitrile was carried out with Catalyst C [having a composition, in terms of atomic ratio, of: $Fe_{12.5}Sb_{25}Cu_{3.5}Te_{1.5}Mo_{1.0}O_{78.25}(SiO_2)_{60}$] under the same condition above. The Catalyst C comprises 90% or more of the particles having a particle diameter in the range of 10 to 200 $\mu$m. The bulk density of the catalyst, the results of the attrition test according to the ACC method, and the results of the crushing strength test according to the present invention, and the catalyst loss are shown in Table 2.

TABLE 2

| Catalyst | Bulk density [g/ml] | Attrition test*(1) | Crushing strength test*(2) | Catalyst loss [kg/t · AN]*(3) |
|---|---|---|---|---|
| C | 1.08 | 0.5 | content of 20 to 75 μm particles having a crushing strength of 0.001 × d² [g-weight/particle] or more: 62% | 1.8 |

The result of the attrition test of the Catalyst C is equivalent to that of of the Catalyst A in Example 1, but the catalyst loss of the Catalyst C is remarkably higher and 3 times or more of that of the Catalyst A.

The Catalyst C used in this comparative example was prepared as follows.

Catalyst C (corresponding to Empirical formula (1)):

In the same manner as for the Catalyst A except that the slurry was mixed thoroughly with an anchor puddle type stirrer, pH was adjusted to 1.5. The slurry is heated to 90° C. for 1 hour with thorough stirring in a stainless steel vessel equipped with a reflux condenser. Spray-drying is carried out at an outlet temperature of 190° C., and the product is calcined at 400° C. for 2 hours and finally in air at 760° C. for 3 hours in a tunnel furnace.

EXAMPLE 2

The synthetic reaction of acrylonitrile by the ammoxidation of propylene was carried out with Catalyst D [composition (atomic ratio) :$P_{1.0}K_{0.2}Mo_{10}Bi_{1.5}Fe_{6.5}Sb_5Ni_6O_{63.1}(SiO_2)_{50}$] under the same conditions as in Example 1. The Catalyst D comprises 90% or more of the particles having a particle diameter in the range of 10 to 200 μm. The bulk density of the catalyst, the results of the attrition test according to the ACC method, and the results of the crushing strength test according to the present invention, and the catalyst loss are shown in Table 3.

TABLE 3

| Catalyst | Bulk density [g/ml] | Attrition test*(1) | Crushing strength test*(2) | Catalyst loss [kg/t · AN]*(3) |
|---|---|---|---|---|
| D | 0.94 | 0.9 | content of 20 to 75 μm particles having a crushing strength of 0.001 × d² [g-weight/particle] or more: 93% | 0.5 |

The Catalyst D was prepared as follows.

Catalyst D (corresponding to Empirical formula (2)):

3.06 kg of potassium nitrate is dissolved in 30.6 liters of water, and 2272 kg of silica sol ($SiO_2$, 20% by weight) is added to the solution. (I)

267 kg of ammonium paramolybdate is dissolved in 670 liters of water at 80° C. (II)

264 kg of nickel nitrate is dissolved in 270 liters of water. (III)

91.7 kg of iron nitrate and 23.8 kg of citric acid are dissolved in 95 liters of water. (IV)

110 kg of bismuth nitrate is dissolved in 110 liters of 10% nitric acid. (V)

(II), (III), (IV) and (V) are added to (I) in this sequence, and 17.4 kg of orthophosphoric acid (content 85% by weight) is further added. Next, pH was adjusted to 8 by adding 15% aqueous ammonia. (VI)

The slurry thus obtained is stirred thoroughly and heated to 100° for 1 hour in a stainless steel pan equipped with a reflux condenser. (VII)

177 kg of iron antimonate powder which has been separately prepared with iron nitrate and antimony trioxide is added, and the mixture is stirred thoroughly under the irradiation of ultrasonic wave. (VIII)

Next, the slurry is spray-dried with a spray-drier. (IX)

Fine spherical particles thus obtained are calcined at 250° C. for 8 hours, then at 400° C. for 25 hours, finally calcined in air at 580° C. for 3 hours in fluidized bed calciner.

EXAMPLE 3

The synthetic reaction of hydrogen cyanide (HCN) by the ammoxidation of methanol was carried out with Catalyst E [composition (atomic ratio):$Fe_{10}Sb_{20}P_{10}Mo_{0.2}V_{0.3}Ni_2Cu_2Te_{0.1}O_{85.55}(SiO_2)_{60}$] in a fluidized bed reactor having a diameter of 1 m. The Catalyst E comprise 90% or more of the particles having a particle size in the range of 10 to 200 μm. The bulk density of the catalyst, the results of the attrition test according to the ACC method, and the results of the crushing strength test according to the present invention, and the catalyst loss are shown in Table 4.

The Catalyst E (corresponding to Empirical formula (1)) was prepared in the similar manner to that for the Catalyst A, except that ammonium metavanadate dissolved in water was added after the addition of ammonium parabolybdate, and, nickel nitrate dissolved in water was added before the addition of ammonium paramolybdate, and orthophosphoric acid was added to the slurry after the heat treatment, to prepare a slurry prior to spray-drying.

Also, the calcination was finally carried out in air at 800° C. for 3 hours in a fluidized bed calciner.

TABLE 4

| Catalyst | Bulk density [g/ml] | Attrition test*(1) | Crushing strength test*(2) | Catalyst loss [kg/t · HCN]*(3) |
|---|---|---|---|---|
| E | 1.17 | 0.5 | content of 20 to 75 μm particles having a crushing strength of 0.001 × d² [g-weight/particle] or more: 98% | 0.1 |

EXAMPLE 4

The synthetic reaction of benzonitrile (BzCN) by the ammoxidation of toluene was carried out with Catalyst F [composition (atomic ratio): $Fe_{11}Sb_{18}V_5Mo_{1.5}W_{0.5}Bi_1O_{72.5}(SiO_2)_{50}$] in a fluidized bed reactor having a diameter of 1 m. The Catalyst F comprises 90% or more of the particles having a particle size in the range of 10 to 200 μm. The bulk density of the catalyst, the results of the attrition test according to the ACC method, and the results of the crushing strength test according to the present invention, and the catalyst loss are shown in Table 5.

The catalyst F was prepared in the similar manner to that for the catalyst A, except that cupper and tellurium were not used, bismuth nitrate was suspended in water and added after the addition of antimony trioxide, and the pH of the slurry was adjusted and subjected to heat treatment. To the slurry after the heat treatment was added ammonium paramolybdate, ammonium metavanadate dissolved in an aqueous oxalic acid solution was added, and ammonium metatungstate dissolved in water was added. The mixture was then subjected to spray-drying.

Also, the calcination of the slurry was finally carried out in air at 800° C. for 3 hours in a fluidized bed calciner.

TABLE 5

| Catalyst | Bulk density [g/ml] | Attrition test*(1) | Crushing strength test*(2) | Catalyst loss [kg/t · B$_2$CN]* (3) |
|---|---|---|---|---|
| F | 1.08 | 0.6 | content of 20 to 75 μm particles having a crushing strength of 0.001 × d$^2$ [g-weight/particle] or more: 95% | 0.3 |

[Evaluation method]

The attrition test and crushing strength test of the catalysts in Examples and a Comparative Example were carried out according to the following methods (1) and (2).

In addition, catalyst loss is an amount defined in the method (3) below.

*(1) Attrition test

Attrition test was carried out according to the method described in "The Method for Synthetic Fluid Cracking Catalyst", American Cyanamid Co., Ltd., 6/31-4m-1/57 which is known as a method for testing a fluidized catalytic cracking catalyst.

Attrition loss (%) R was obtained from the following equation:

$$\text{Attrition loss } (\%) R \frac{B}{C-A} \times 100$$

wherein
A=weight of a catalyst lost by attrition in 5 hours (g),
B=weight of a catalyst lost by attrition in 5–20 hours (g),
C=weight of a catalyst subjected to the test (g).
The test was carried out under the condition of C=50 (g).

When a catalyst ha s a higher attrition-resistance, i.e. a catalyst has a larger strength, the attrition loss (%) R becomes smaller.

*(2) Crushing strength test

It was carried out for 100 catalyst particles sampled randomly from the particulate catalyst of 20 to 75 μm screened through Micro Mesh High Precision Sieves, manufactured by Buckbee Mears Co. St. Paul, U. S. A., with "Shimadzu MCTM-200", manufactured by Shimadzu Seisakusho, Ltd. Japan under the following determining conditions.

Indenter
Upper pressurizing indenter, 500 μm plain indenter made of diamond;
Lower pressurizing plate, SUS plate;
Loading rate: 0.72 g weight/sec.

In addition, the average of the length and the breadth is considered as the particle diameter d, when the particle is not spherical.

*(3) Catalyst loss

Catalyst loss is a loss of catalyst (kg) per production amount (t) of a product in question.

In conclusion, as described in the paragraph of "SUMMARY OF THE INVENTION", the catalyst loss of a fluidized bed catalyst can be reduced, the particle size distribution of the fluidized bed catalyst can be thus maintained in a proper range, and the reaction can be maintained at a high level without lowering the contact efficiency according to the present invention.

What is claimed is:

1. A particulate catalyst, which comprises catalyst particles of which 90% or more are in the range of 5 to 500 μm on the weight-based particle size distribution and 90% or more of the 20 to 75 μm particles have a crushing strength in terms of breaking load which satisfies the following equation:

$$CS > A \cdot d^\alpha$$

wherein CS represents a crushing strength in terms of a breaking load in g-weight/particle;
A represents a constant 0.001;
d represents a particle diameter in μm; and
α represents a constant 2,
said catalyst being one indicated by one of the following empirical formulas:
Empirical formula (1):

$$Sb_{10}A_aB_bC_cO_x, \text{ atomic ratio}$$

wherein A is at least one element selected from the group consisting of Fe, Co, Ni, Mn, U, Ce, Sn and Cu;
B is at least one element selected from the group consisting of V, Mo and W;
C is at least one element selected from the group consisting of Mg, Ca, Sr, Ba, La, Ti, Zr, Nb, Ta, Cr, Re, Ru, Os, Rh, Ir, Pd, Pt, Ag, Zn, Cd, B, Al, Ga, In, Tl, Ge, Pb, P, As, Bi, Se and Te;
a is 1 to 10;
b is 0 to 5;
c is 0 to 10;
Empirical formula (2):

$$Mo_{10}D_dE_eF_fO_x, \text{ atomic ratio}$$

wherein D is at least one element selected from the group consisting of Fe, Ni, Co, Mn, Cr, Mg, Ca, Cu, Zn, La, Ce, Al and Sn;
E is at least one element selected from the group consisting of Sb, Bi, As, P, B, Te, W and V;
F is at least one element selected from the group consisting of Li, Na, K, Rb and Cs;
d is 0 to 10;
e is 0 to 10;
f is 0 to 3; and
Empirical formula (3):

$$V_{10}G_gH_hO_x, \text{ atomic ratio}$$

wherein G is at least one element selected from the group consisting of Li, Na, K, Rb, Cs, Tl, Mg, Ca, Sr and Ba;
H is at least one element selected from the group consisting of La, Ce, Ti, Zr, Nb, Ta, Cr, Mo, W, Mn, Re, Fe, Ru, Os, Co, Rb, Ir, Ni, Pd, Pt, Cu, Ag, Zn, Cd, B, Al, Ga, In, Ge, Sn, Pb, P, As, Sb, Bi, S, Se and Te;
g is 0 to 5; and
h is 0 to 15;
wherein in the formulae (1) to (3), 0 indicates an oxygen atom, and x indicates the number of the oxygen atoms in the oxide formed by the elements concerned.

2. A fluidized bed of the particulate catalyst according to claim 1.

3. A process which comprises oxidizing an olefin in the presence of a catalyst as claimed in claim 1 to produce a corresponding aldehyde or carboxylic acid.

4. A process which comprises oxidizing an aldehyde in the presence of a catalyst as claimed in claim 1 to produce a corresponding carboxylic acid.

5. A process which comprises oxidizing an olefin, an alcohol or an alkylaromatic hydrocarbon compound in the presence of ammonia and a catalyst as claimed in claim 1 to produce a corresponding nitrile.

6. A process which comprises oxidizing methanol in the presence of ammonia and a catalyst as claimed in claim 1 to produce hydrogen cyanide.

7. The particulate catalyst as claimed in claim 1, wherein the catalyst has the composition represented by the Empirical formula (1).

8. The particulate catalyst as claimed in claim 1, wherein the catalyst has the composition represented by the Empirical formula (2).

9. The particulate catalyst as claimed in claim 1, wherein A in Empirical formula (1) is at least one element selected from the group consisting of Fe, U, Sn and Cu.

10. The particulate catalyst as claimed in claim 1, wherein C in Empirical formula (1) is at least one element selected from the group consisting of Mg, La, Nb, Ag, Zn, B, Pb, P, Bi and Te.

11. The particulate catalyst as claimed in claim 1, wherein D in Empirical formula (2) is at least one element selected from the group consisting of Fe, Ni, Co, Mn, Cr, Mg and Ce.

12. The particulate catalyst as claimed in claim 1, wherein G in Empirical formula (3) is at least one element selected from the group consisting of K, Rb, Cs and Mg.

13. The particulate catalyst as claimed in claim 1, wherein H in Empirical formula (3) is at least one element selected from the group consisting of La, Ce, Nb, Cr, Mo, W, Mn, Fe, Co, Ni, P, Sb, Bi and Te.

14. A process which comprises oxidizing a hydrocarbon or alcohol in the presence of a catalyst as claimed in claim 1.

15. A process which comprises subjecting a hydrocarbon or alcohol to ammoxidation in the presence of a catalyst as claimed in claim 1.

16. A process which comprises subjecting a hydrocarbon to oxidative dehydrogenation in the presence of a catalyst as claimed in claim 1.

17. A process which comprises alkylating a phenol or amine in the presence of a catalyst as claimed in claim 1.

18. A process which comprises dehydrogenating a compound in the presence of a catalyst as claimed in claim 1.

19. A process which comprises hydrogenating a compound in the presence of a catalyst as claimed in claim 1.

20. A process which comprises dehydrating a compound in the presence of a catalyst as claimed in claim 1.

* * * * *